United States Patent [19]
Okazaki et al.

[11] Patent Number: 5,450,848
[45] Date of Patent: Sep. 19, 1995

[54] SHOCKWAVE GENERATING SYSTEM CAPABLE OF DISPLAYING SHOCKWAVE EFFECTIVE REGION

[75] Inventors: Kiyoshi Okazaki, Tochigi; Kaoru Suzuki, Utsunomiya; Shoichi Yamanaka, Kuroiso, all of Japan

[73] Assignee: Kabushiki Kaisha Toshiba, Kawasaki, Japan

[21] Appl. No.: 80,973

[22] Filed: Jun. 24, 1993

Related U.S. Application Data

[63] Continuation of Ser. No. 674,157, Mar. 25, 1991, abandoned.

[30] Foreign Application Priority Data

Mar. 24, 1990 [JP] Japan .................................. 2-074395

[51] Int. Cl.⁶ .............................................. A61B 17/22
[52] U.S. Cl. ..................................... 128/660.03; 601/3; 601/4; 607/97
[58] Field of Search ........ 128/660.03, 24 AA, 24 EL; 607/97; 601/2-4

[56] References Cited

U.S. PATENT DOCUMENTS

| | | | |
|---|---|---|---|
| 4,617,931 | 10/1986 | Dory . | |
| 4,962,754 | 10/1990 | Okazaki | 128/660.03 |
| 4,984,575 | 1/1991 | Uchiyama et al. | 128/660.03 |
| 4,986,275 | 1/1991 | Ishida et al. | 128/660.03 |
| 5,060,634 | 10/1991 | Belikan et al. | 128/660.03 |

FOREIGN PATENT DOCUMENTS

WO87/01927 4/1987 WIPO .

*Primary Examiner*—Ruth S. Smith
*Attorney, Agent, or Firm*—Foley & Lardner

[57] ABSTRACT

In a shockwave generating apparatus, a shockwave effective region pattern is displayed on a B-mode ultrasonic tomographic image of a biological body under superimposition state. The shockwave generating apparatus includes: an imaging cata acqustion unit for imaging an interior area of a biological body under medical examination, containing an object to be removed, thereby to produce image data on the interior area; a shockwave generator for generating shockwaves to be focused onto the object to be destroyed; a position detecting means for detector a focus position of the shockwaves in relation with an image of the interior area so as to obtain positional information on the focus position; an image memory for storing therein data on a shockwave effective region produced by receiving the shockwaves having a predetermined physical value, in which region damage caused by the shockwaves having a predetermined physical value is done to the biological body; and a display units for displaying the image of the interior area based on the image data and a pattern indicative of at least the shockwave effective region based on both the focus position information and the shockwave effective region data, the pattern being superimposed on the image of the interior area of the biological body "BO".

13 Claims, 12 Drawing Sheets

| ///// | 1st GRADATION |
| ----- | ----- |
| \\\\\ | SECOND GRADATION |

| ‖‖‖‖‖ | OPPOSITE BLACK AND WHITE |
| ----- | ----- |
| ≡≡≡≡≡ | BLACK AND WHITE |

| ≡≡≡≡≡ | YELLOW AND BLACK |
| ----- | ----- |
| \\\\\ | OTHER COLORS |

SHOCKWAVE GENERATING SYSTEM CAPABLE OF DISPLAYING SHOCKWAVE EFFECTIVE REGION

This application is a continuation of application Ser. No. 07/674,157, filed Mar. 25, 1991, now abandoned.

BACKGROUND OF THE INVENTION

FIELD OF THE INVENTION

The present invention relates to a shockwave generating apparatus for generating shockwaves so as to disintegrate an object (calculus) to be removed present in a biological body by focused energy of the shockwaves, while displaying a shockwave effective region. The function of the instant invention may be loosely referred to as "curing" which means to remove or destroy unwanted calculus.

The present invention also relates to a hyperthermia apparatus capable of destroying a cancer tissue and the like with heating effects caused by a continuous ultrasonic wave for a removing purpose.

Various types of hyperthermia apparatuses or ultrasonic shockwave generating apparatuses capable of disintegrating an object such as a calculus, have been developed and commercially available, e.g., known from U.S. Pat. No. 4,617,931 entitled "ULTRASONIC PULSE APPARATUS FOR DESTROYING CALCULUSES" to Dory issued on Oct. 21, 1986. In this ultrasonic pulse apparatus, the ultrasonic pulse applicator with the through hole at a center position thereof is employed. Both the transducers formed in a concave shape and also the imaging ultrasonic probe are arranged in the ultrasonic pulse applicator.

This ultrasonic pulse apparatus is operable under two different functions, i.e., the ultrasonic (shockwave) apparatus and hyperthermia apparatus.

When a calculus present in a biological body under medical examination is disintegrated by employing the above-described ultrasonic pulse apparatus, a focal point or focus position of shock waves generated by utilizing the ultrasonic pulses must be positionally coincident with the calculus, which will be referred to "a focal-point positioning" in the specification. The focal-point positioning of Dory U.S. Patent is performed as follows. A B-mode image (tomographic image) of a biological body is displayed by processing B-mode ultrasonic image data acquired by the imaging probe on the display screen of the display unit, and also the focal point marker, e.g., the cross marker representative of the focal point for the shock waves or continuous ultrasonic wave is superimposed on the above-described B-mode image. Under such a display condition, this cross-shaped focal point marker is positionally made coincident with the image of the calculus on the display screen. It should be noted that this marker indicates the focal point geometrically determined by the concave surface of the destroying transducer elements. Then the focal-point positioning is properly realized.

However, the above-described conventional focal-point positioning by way of the marker superimposed on the B-mode image can merely provide positional information indicative of the peak pressure of the shockwaves, or continuous ultrasonic wave, but gives no information on the effective region, or range of these waves, in which the biological body is subjected to the medical effects caused by the shockwaves and/or continuous ultrasonic wave. That is to say, as is known in the medical field, a shape of such an effective region caused by the shockwaves and/or continuous ultrasonic wave is not a point (e.g., not a pin point), but an area with a center of this point (will be referred to as an "effective region"). A dimension of this effective region by the shockwaves and/or continuous ultrasonic wave is determined by a method for generating shockwaves and also by a diameter of an overall spherical surface formed by the removing transducer elements. The above-described difficulties of the conventional focal-point marker display method will now be described more in detail. That is, if such a focal point marker displayed on the display screen is positioned at an end portion of a biological body to be destroyed, the medical effects caused by the shockwaves or continuous ultrasonic wave may give adverse influences to a normal biological tissue around this marked end position of the biological body, and may cause harmful side effects thereon. There is another drawback that if the size of this effective region is greater than that of the object to be destroyed, the actual medical influences caused by the shockwaves or continuous ultrasonic wave may be given to the normal biological tissue around this object to be destroyed, so that the area defined by this normal biological tissue may be medically damaged. Apparently, this area is not medically damaged as long as it is viewed on the display screen. This also induces medically harm or medical unsafe treatments.

The present invention has been made in an attempt to solve the above-described drawbacks of the marking system, and therefore, has an object to provide a shockwave generating apparatus and a hyperthermia apparatus with a shockwave/ultrasonic effective region marking (patterning) system, capable of performing a safety diagnosis.

SUMMARY OF THE INVENTION

To achieve the above-described object and other features of the present invention, a shockwave generating apparatus comprises:

imaging means (20:40:3) for imaging an interior area of a biological body (BO) under medical examination, containing an object (9) to be destroyed, thereby to produce image data on the interior area;

shockwave generating means (12:50) for generating shockwaves (26) to be focused onto the object (9) to be cured;

position detecting means for detecting a focus position (30) of the shockwaves (26) in relation with an image of the interior area so as to obtain positional information on the focus position (30);

storage means (46B) for storing therein data on a shockwave effective region (Eh) produced by receiving the shockwaves (26) having a predetermined physical value, in which region a medical influence caused by said shockwaves (26) having a predetermined physical value is given to the biological body (BO); and, display means (80) for displaying said image of the interior area based on said image data, and also a pattern $(M_1:M_7:M_{11}:M_{31})$ indicative of at least said shockwave effective region (Eh) based on both said focus position information and said shockwave effective region data, said pattern $(M_1:M_7:M_{11}:M_{13})$ being superimposed on said image of the interior area of the biological body "BO".

BRIEF DESCRIPTION OF THE DRAWINGS

For a better understanding of the present invention, reference is made to the following descriptions in conjunction with the accompanying drawings, in which.

DETAILED DESCRIPTION OF PREFERRED EMBODIMENTS

OVERALL ARRANGEMENT OF SHOCKWAVE GENERATING APPARATUS

Figure 1:
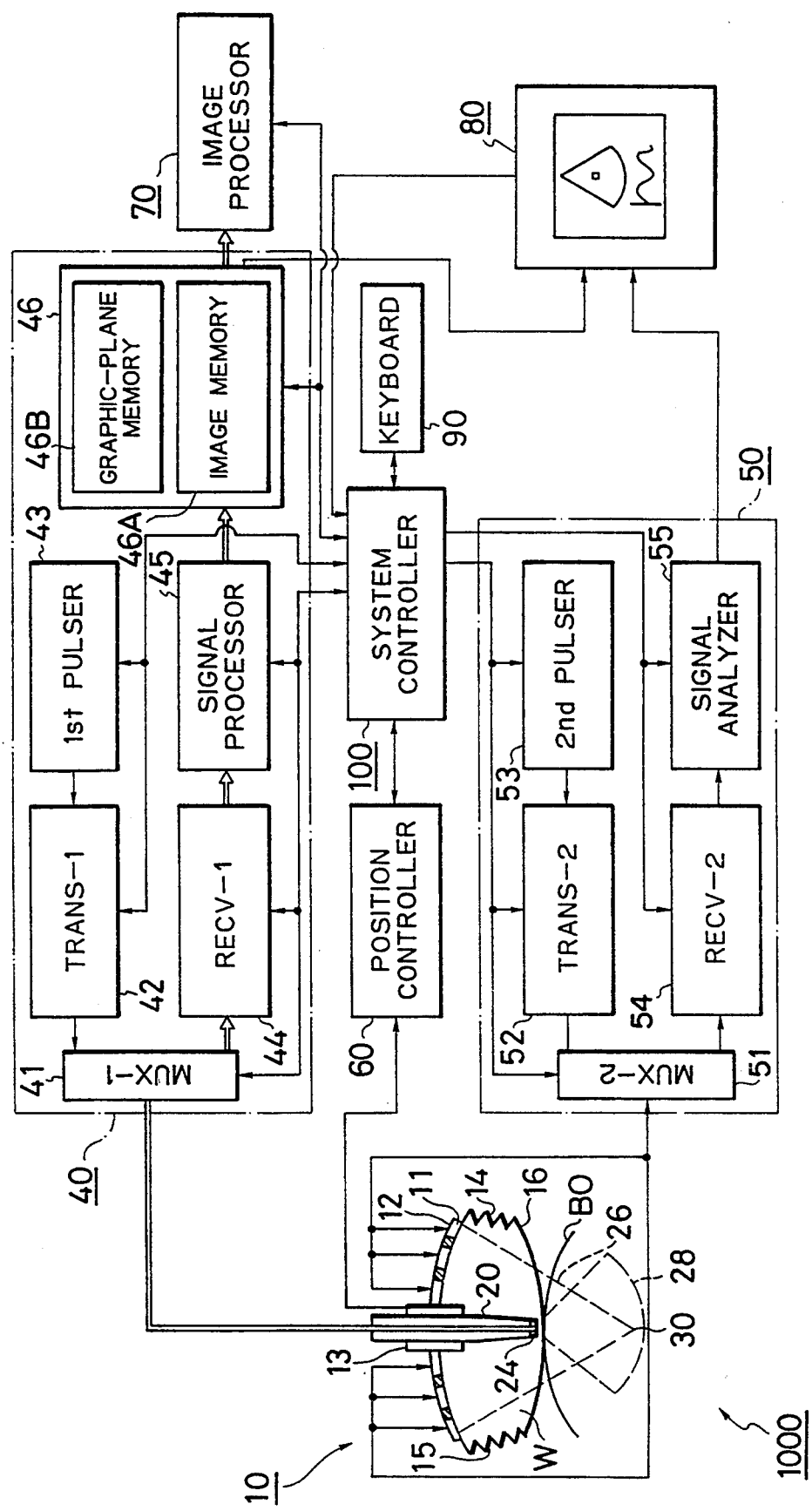
FIG. 1 is a schematic block diagram for showing an arrangement of a shockwave generating apparatus 1000 according to a first preferred embodiment of the present invention.

An overall arrangement of a shockwave generating apparatus 1000, according to a first preferred embodiment of the present invention, will now be described with reference to FIG. 1.

The shockwave generating apparatus 1000 mainly includes: a shockwave applicator 10 equipped with an ultrasonic imaging probe 20 functioning as an ultrasonic imaging means; a B-mode image data acquisition unit 40 functioning as an ultrasonic imaging means to obtain a B-mode image of a biological body "BO" with employment of the imaging probe 20; a shockwave generation unit 50 for generating shockwaves to be focused onto the biological body "BO" in order to disintegrate an object to be destroyed, for instance, a calculus; an image processing unit 70 for processing the B-mode image data acquired by the B-mode image data acquisition unit 40; a display unit 80 for displaying both the B-mode image (tomographic image) of the biological body "BO" as a fan-shaped sound field 28 and an effective region marker corresponding to a focal point 30 of shockwaves 26 under super imposition condition; and also a system controller 100 for mainly controlling transmission/reception timings of various signals appearing in the above-described units, and further controlling amplitudes and frequencies of the ultrasonic pulses. The shockwave generating apparatus 1000 further includes a position controller 60 for controlling positioning conditions of the shockwave applicator 10 under control of the system controller 100; and a keyboard 90 for entering various data on destroying conditions.

A detailed construction of the above-described shockwave applicator 10 is as follows. A shockwave transducer 12 is so arranged that a plurality of curing transducer elements subdivided into a coaxial form are formed in a concave shape. A transport section 13 supports the imaging probe 20 in a movable fashion along a longitudinal direction thereof through a central opening portion of the above-described shockwave transducer 12, and includes a position detecting means such as a potentiometer, for detecting a relative position between the image probe 20 and the shockwave transducer 12. Furthermore, a water bag 14 is positioned at a transmission side of ultrasonic pulses of the shockwave transducer 12 and is filled with water "W" functioning as an ultrasonic transmitting medium for the shockwaves. This water bag 14 is formed by a bellows 15 around this bag and also a thin film at a bottom 16 thereof, which has an acoustic impedance substantially equal to that of water "W".

The B-mode image data acquisition unit 40 includes: a first multiplexer (MUX-1) 41, a first transmitter circuit (TRANS-1) 42; a first pulser (1st PULSER) 43; a first receiver circuit (RECV-1) 44; a signal processor 45; and a memory circuit 46. The first multiplexer 41 sequentially scans a plurality of (imaging) transducer elements provided at a tip portion of the imaging probe 20 so as to project ultrasonic pulses and also receive ultrasonic echoes reflected from an interior of the biological body "BO" (namely, B-mode scanning). The first transmitter circuit 42 transmits energizing pulse signals to the imaging probe 20 via the first multiplexer 41 in response to pulse signals derived from the first pulser 43. The echo signals are received via the imaging probe 20 and first multiplexer 41 by the first receiver circuit 44. The signal processor circuit 45 amplitude-detects the output signal from the first receiver circuit 44 thereby to obtain a video (image) signal of the interior portion of the biological body "BO".

The memory circuit 46 is constructed of an image memory 46A and a graphic-plane memory 46B.

The shockwave generation unit 50 includes: a second multiplexer (MUX-2) 51 for sequentially scanning a (destroying) transducer group 11 of the shockwave transducer 12; a second transmitter circuit (TRANS-2) 52 for transmitting energizing pulse signals via the second multiplexer 51 to the shockwave transducer 12 in response to pulse signals derived from a second pulser 53 in order that the shockwave transducer 12 can project the pulsatory ultrasonic waves to a focal point 30 at which shockwaves 26 may be generated; a second receiver (RECV-2) 54 for receiving echo signals from the shockwave transducer 12; and a signal analyzer circuit (SIGNAL ANALYZER) 55 for performing a predetermined signal analysis with respect to the output signal from the second receiver circuit 54.

As previously described, the memory circuit 46 includes the graphic-plane memory 46B. The graphic-plane memory 46B stores therein data on an effective region pattern "M$_1$" which indicates a region of the biological body "BO" may be effected by the shockwaves. This effective region pattern "M$_1$" is superimposed on the B-mode image of this biological body "BO" displayed on the display screen of the display unit 80.

GENERATION OF EFFECTIVE REGION PATTERN "$M_1$"

A generation of data on the effective region pattern "$M_1$" stored in the graphic-plane memory 46B will now be explained.

Figure 2:
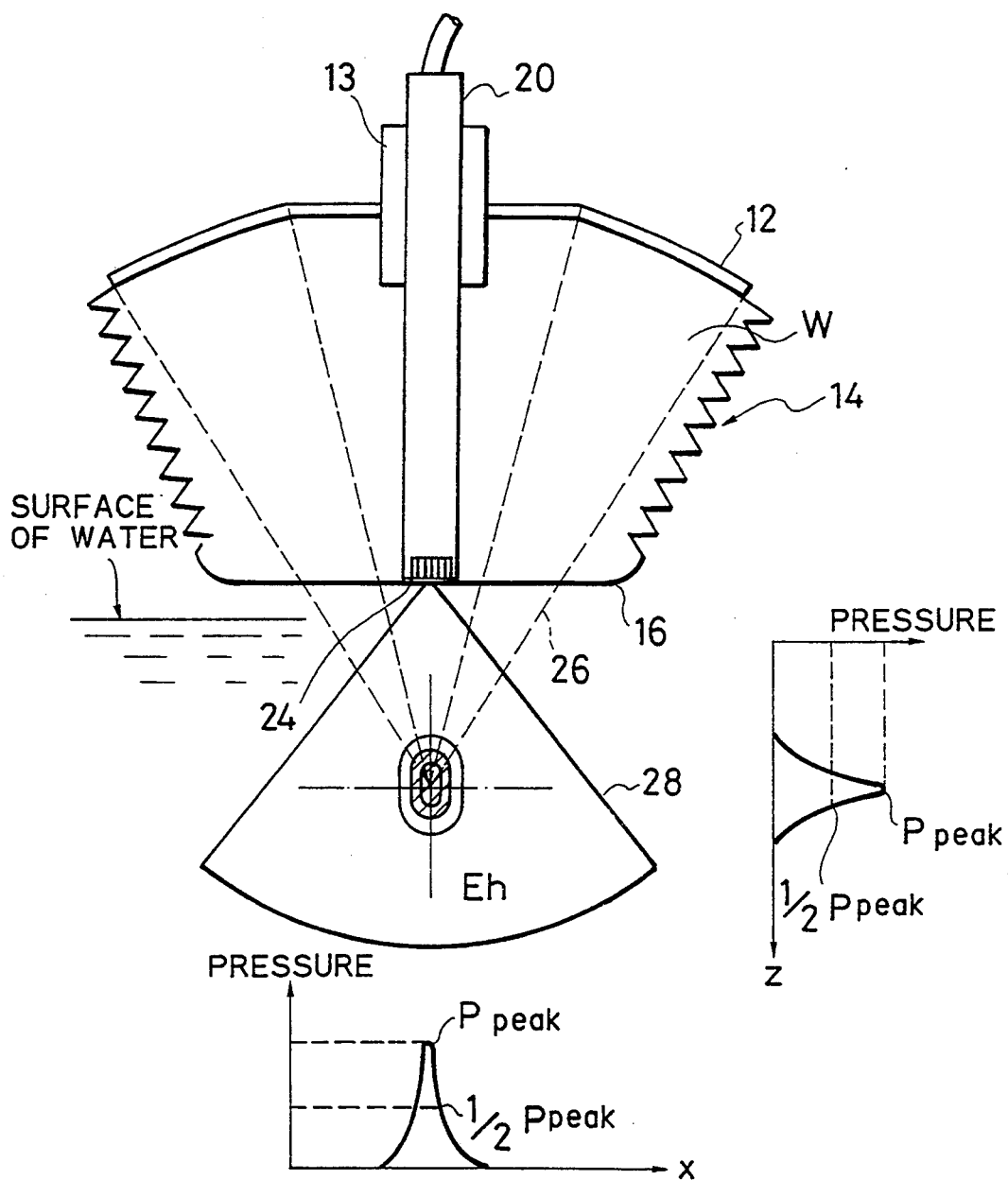
FIG. 2 is an illustration of pressure distributions produced by shockwaves for explaining a basic idea of an effective region display system employed in the shockwave generating apparatus 1000 shown in FIG. 1.
Figure 3A:
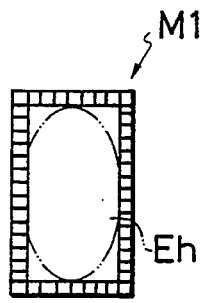
FIGS. 3A–3G schematically represent the focal-point positioning between a B-mode image and various effective region patterns displayed in the monitor of the shockwave generating apparatus 1000.

FIG. 2 represents pressure distributions of the shockwaves 26 produced by the shockwave transducer 12 shown in FIG. 1, which is practically obtained by the known sound field measuring method. In accordance with this practical sound field measuring method, data on pressures of shockwaves are acquired in the two-dimensional coordinate system of X and Z directions, depending upon the position of the shockwave transducer 12, by utilizing a hydrophone (not shown in detail) having a piezoelectric element (not shown either) at a tip portion thereof and positioned into water. Then, a region indicative of, for instance, a half of maximum pressure "P peak" of thus acquired pressure data, is understood as the above-described "shockwave effective region (Eh)" where the shockwaves may give medical effects or influences to the biological body "BO". A contour of a rectangular region with a transverse length of about 3 to 5 mm and a longitudinal length of about 20 to 30 mm, involving this shockwave effective region "Eh" is defined as the shockwave effective region pattern "$M_1$" displayed in white, as illustrated in FIG. 3A, and is stored as graphic plane (two-dimensional) data in the graphic-plane memory 46B.

Figure 4:
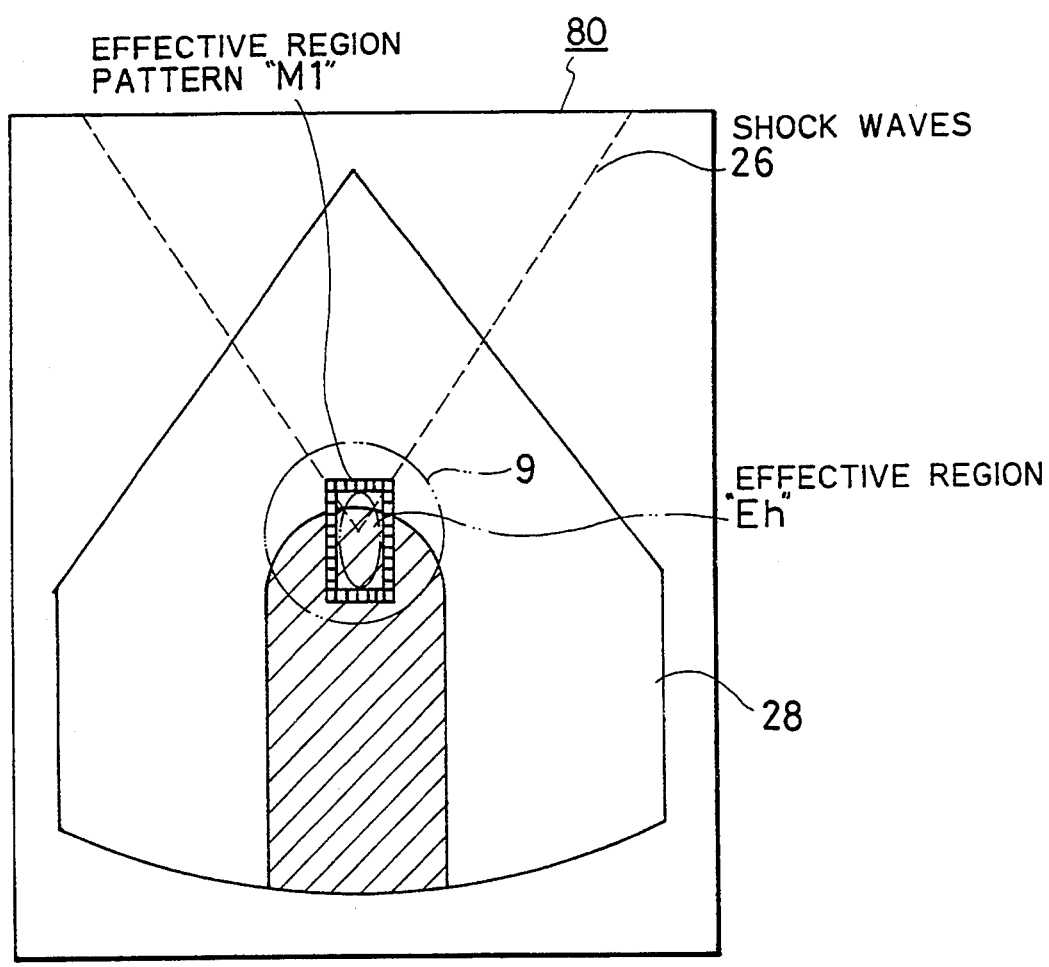
FIG. 4 illustrate a relative relationship between the effective region "Eh" and the object to be destroyed.

FIG. 4 schematically illustrates one display example of the display unit 80. On this display screen, a renal calculus 9 is displayed at a center thereof by a circular shape, as indicated by a two-dot/dash line. An upper portion of this renal calculus 9 strongly reflects the incoming ultrasonic pulses from the imaging probe 20, is observed as a white specific shape, whereas a lower portion thereof is shadowed and thus observed in a black shape as indicated by a hatching line.

OVERALL OPERATION OF SHOCKWAVE GENERATING APPARATUS

An overall operation of the shockwave generating apparatus 1000 will now be described with reference to FIGS. 1 to 4.

First, an operator sets the shockwave applicator 10 in such a manner that the bottom 16 of the water bag 14 of this applicator 10 is in contact with a surface of the biological body "BO", as illustrated in FIG. 1. Under this condition, the tip portion of the imaging probe 20 is in contact with the bottom 16 of this water bag 14.

Next, the operator performs the B-mode ultrasonic imaging by way of the imaging probe 20 in order that as shown in FIG. 4, for instance, an image of the renal calculus 9 having a substantially circular shape with approximately 10 mm is displayed on the display screen of the display unit 80.

Subsequently, the operator enters various data required for the positional control of the shockwave transducer 12 under control of the positional controller 60 into the keyboard 90 in order that a center of the above-described shockwave effective region pattern "$M_1$" is positionally made coincident with a center of the renal calculus 9 displayed on the display screen of the display unit 80. In this case, the shockwave effective region pattern "$M_1$" displayed in the display screen is moved in accordance with the movement of the shockwave transducer 12 under control of the main controller 100.

When the center of this shockwave effective region pattern "$M_1$" has been made positionally coincident with the center of the renal calculus 9, as represented in FIG. 4, the operator again instructs via the keyboard 90 such that the destroying transducer group 11 of the shockwave transducer 12 is excited by the second pulser 53 employed in the shockwave generation unit 50, whereby the renal calculus 9 may be disintegrated.

As previously stated, the first shockwave generating apparatus 1000 has the particular advantages that since the shockwave effective region "$M_1$" superimposed on the B-mode tomographic image of the biological body "BO" on the display screen, contains the shockwave effective region "Eh", unwanted shockwave applications to any portion other than the portion to be destroyed of the biological body "BO" may be avoided. Moreover, this effective region pattern "$M_1$" is readily distinguishable from both the B-mode image and the image of the portion to be destroyed, e.g., renal calculus 9.

DISPLAY METHOD FOR SHOCKWAVE EFFECTIVE REGION PATTERNS

Referring back to FIGS. 3A to 3G, display methods for the various shockwave effective region patterns "$M_1$" to "$M_7$" will now be described more in detail.

These pattern display methods constitutes a major feature of the present invention.

Before describing the pattern display methods in detail, various forms of the shockwave effective region patterns (markers) "$M_1$" through "$M_7$" will now be briefly explained.

Figure 3B:
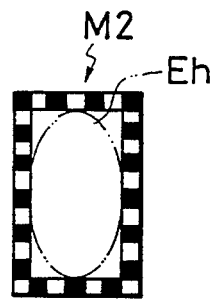

In FIG. 3B, there is shown an effective region pattern (marker) "$M_2$". This pattern "$M_2$" represents a contour of the shockwave effective region "Eh", which is similar to the first effective region pattern "$M_1$". This contour is displayed as a black/white alternating pattern. As a result, since the calculus image in the B-mode tomographic image represents higher gradation than that of other image portions, a marker with a only white pattern may be mistakenly recognized. Conversely, since the biological body represents lower gradation, another marker with a only black pattern is not distinguishable. Therefore, such a marker "$M_2$" with the black/white patterns is very distinguishable from other images.

Figure 3C:
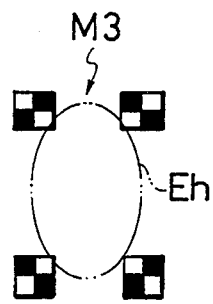

FIG. 3C illustrates a third effective region pattern (marker) "$M_3$" in which four sets of black/white combination patterns are arranged at all corners of a rectangular shape.

Figure 3D:
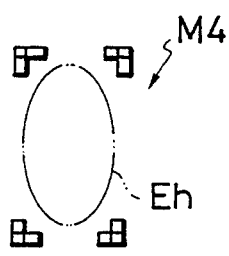

FIG. 3D represents a fourth effective region pattern "$M_4$" in which four sets of white patterns are arranged at all corners of a rectangular shape.

Figure 3E:
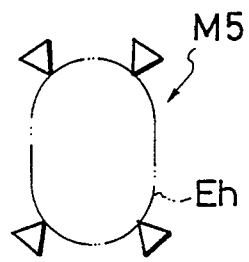

FIG. 3E indicates a fifth effective four sets of triangular white patterns are arranged at all corners of a rectangular shape.

Figure 3F:
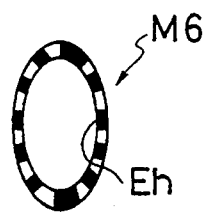

FIG. 3F illustrates a sixth effective region pattern "$M_6$", the entire shape of which corresponds to the outer shape of the effective region "Eh", and the contour of which is formed by a black/white alternating pattern.

Figure 3G:
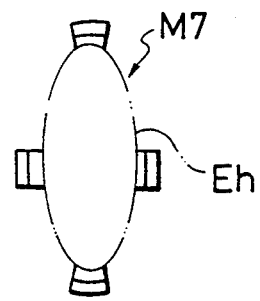

Further, FIG. 3G represents a seventh effective region pattern "$M_7$", the entire shape of which corresponds to the outer shape of the elliptic effective region "Eh", and the contour of which is formed by arranging four sets of black/white patterns around the elliptic effective region "Eh".

Figure 5A:
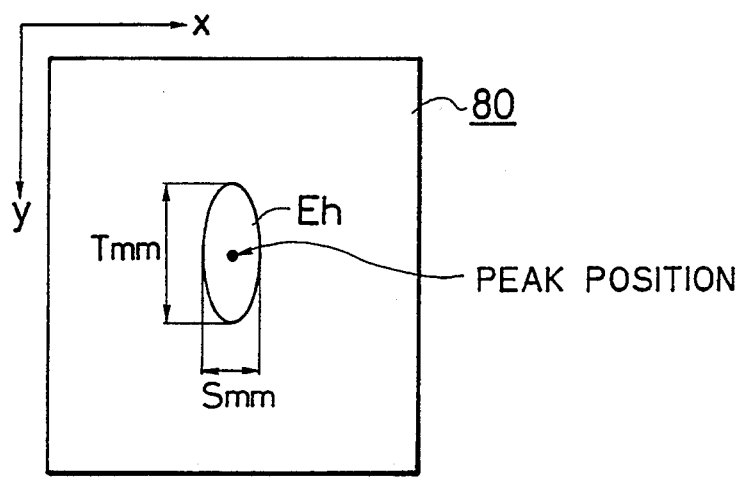
FIGS. 5A to 5C pictorically represent how to display the shockwave effective region patterns.
Figure 5B:
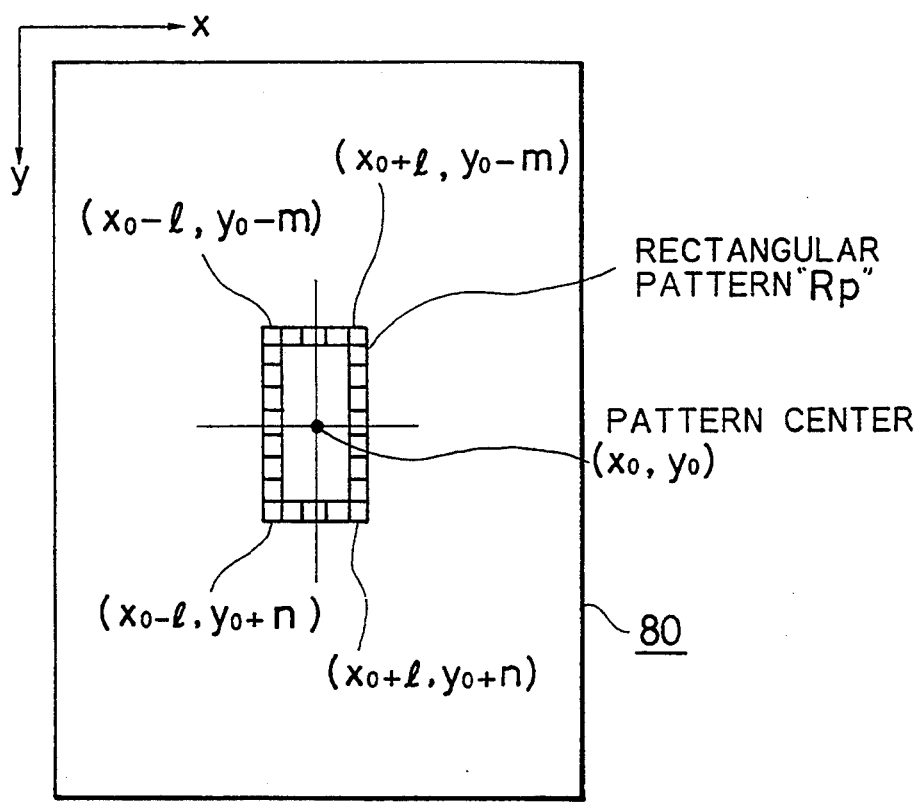
Figure 5C:
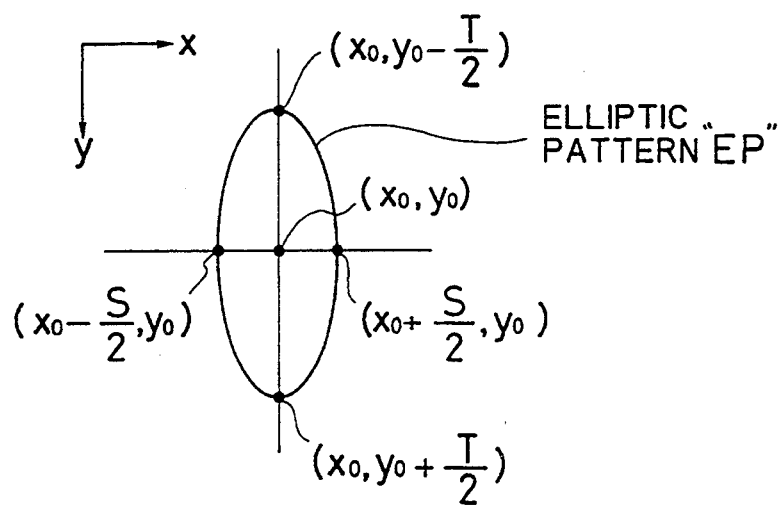

Referring now to FIGS. 5A to 5C, the display methods of these shockwave effective region patterns or markers will now be described more in detail.

FIG. 5A and 5B illustrate how to display the first shockwave effective region pattern (marker) "$M_1$".

As shown in FIG. 5A, it is assumed that the effective region "Eh" has been previously measured by the above-described known sound field measuring apparatus (not shown). A longitudinal length of this effective region "Eh" is selected to be "T" mm, whereas a transverse length thereof is selected to be "S" mm.

Subsequently, as represented in FIG. 5B, pixels of a rectangular pattern "Rp" substantially identical to the above-described effective region "Eh" are determined in accordance with the following equation (1):

$$S = (2l+1) \times \Delta x \quad T = (2m+1) \times \Delta y \tag{1}$$

An area defined by multiplying (2l+1) pixels in the X-direction by (m+n) pixels in the Y-direction corresponds the desirable first effective region pattern or marker "$M_1$". Symbols "l", "m", "n" indicate shift amounts with respective to the center position ($x_o$, $y_o$).

In the system controller 100, data on a center position ($x_o$, $y_o$) of the rectangular effective region pattern "Rc" is supplied from the position controller 60, so that the system controller 100 generates the rectangular shockwave effective pattern "$M_1$" on the corresponding position of the display screen and also stores this pattern data in the graphic-plane memory 46B.

Then, both the B-mode tomographic image of the biological body "BO" and the first shockwave effective region marker "$M_1$" when the above-described data on the rectangular pattern generated by the main controller 100 is entered into the graphic-plane memory 64B are displayed on the display screen of the display unit 80 under superimposition state.

As apparent from the foregoing description, when the position ($x_o'$, $y_o'$) of the position controller 60 is changed, the rectangular effective region pattern "$M_1$" is positionally shifted to the corresponding display position. In other words, when the presently appearing pattern "$M_1$" is moved by an operator, the positional data on this rectangular effective region pattern "$M_1$" are rewritten in the graphic-plane memory 46B under control of the main controller 100, whereby this rectangular effective region pattern "$M_1$" is newly displayed on the desirable (corresponding) display position based on the rewritten positional data.

Furthermore, FIG. 5C illustrates an elliptic shockwave effective region pattern "EP" similar to the sixth effective region pattern "$M_e$" shown in FIG. 3F. In this case, this elliptic pattern "EP" is calculated by satisfying the following equation (2):

$$\frac{2^2}{S}(x - x_o)^2 + \frac{2^2}{T}(y - y_o)^2 = 1 \tag{2}$$

Figure 6A:
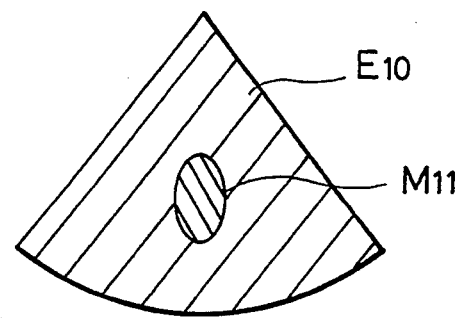
FIGS. 6A to 6C pictorically represent other shockwave effective region patterns.
Figure 6B:
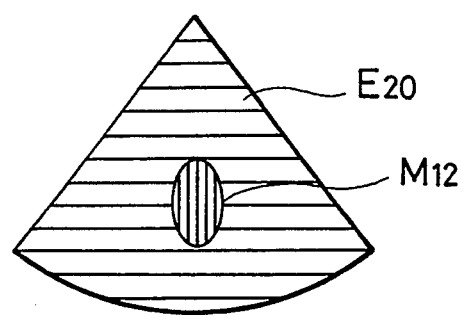
Figure 6C:
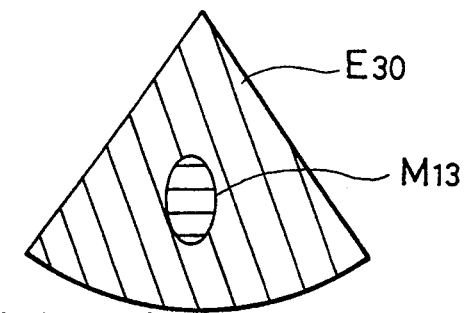

In FIGS. 6A to 6C, there are shown other shockwave effective region patterns "$M_{11}$" to "$M_{13}$" having different features from those of the above-described patterns "$M_1$" to "$M_7$" represented in FIGS. 3A to 3G.

The pattern "$M_{11}$" shown in FIG. 6A has such a feature that an overall region of this pattern "$M_{11}$" is displayed with different gradation from that of other region "$E_{10}$". For instance, assuming now that the gradation of the B-mode image data is represented by the gradation from "O" to "A", and also gradation of a certain point within the region "$E_{10}$" is defined as "B" gradation of a pattern "$M_{11}$" may be defined as "B+C".

The pattern "$M_{12}$" is shown in FIG. 6B in such a manner that the black/white representation of the overall area of this pattern "$M_{12}$" is set to be opposite to that of other regions "$E_{20}$". For example, when the gradation of the B-mode image data is represented by "O" to "A", and also gradation of a certain point of the region "$E_{20}$" is defined as "B", the gradation of this pattern "$M_{12}$" may be defined as "A-B".

The effective region pattern "$M_{13}$" shown in FIG. 6C has such a particular feature that an overall region of this pattern "$M_{13}$" is represented in yellow and black, whereas the region "$E_{30}$" is represented in any colors other than black/white yellow/black.

As apparent from the foregoing descriptions, these effective region patterns "$M_{11}$" to "$M_{13}$" have similar advantages to those of the first to seventh effective region patterns "$M_1$" to "$M_7$".

Now, a detailed description will be made how to display these effective region patterns "$M_{11}$" to "$M_{13}$" with reference to FIGS. 7A and 7B.

Figure 7A:
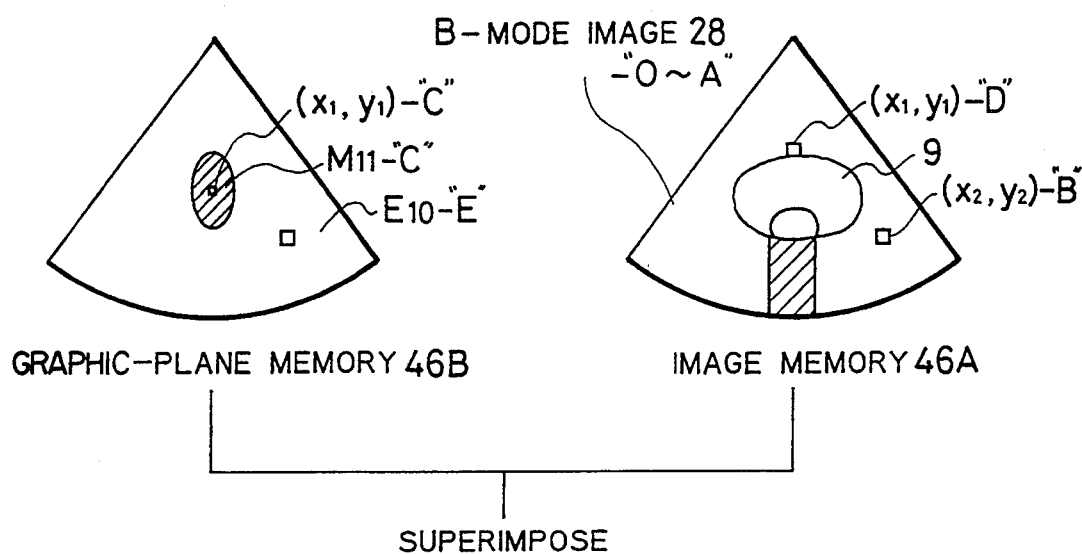
FIGS. 7A and 7B pictorically illustrate how to display other effective region patterns.

In FIG. 7A, data on a left image is stored in the graphic-plane memory 46B, and data on a right image is stored in the image memory 46A. The gradation of first pixel point ($x_1$, $y_1$) is set to "C". The gradation of the effective region pattern "$M_{11}$" is also set to "C", and also the gradation of the region "$E_{10}$" is set to "E", as illustrated in the leftside view of FIG. 7A. If the gradation of the first pixel point ($x_1$, $y_1$) is selected to be "D" shown in the rightside view of FIG. 7A, the gradation of the second pixel point ($x_2$, $y_2$) is set to "B", whereas the gradation of the B-mode image 28 is set to "O" through "A".

When these memory data on the left/right patterns are superimposed with each other, the first pixel point ($x_1$, $y_1$) has the resultant gradation of (D+C) within the effective region pattern "$M_{11}$". On the other hand, the resultant gradation of the second pixel point ($x_2$, $y_2$) becomes "B-E" within the region "$E_{10}$". As a consequence, the effective region may be observed in a bright condition.

When displaying the effective region pattern "$M_{12}$" as shown in FIG. 6B, the gradation of the pixel position within the pattern "$M_{12}$" is set to "D", whereas the present gradation "B" of the pixel position within the region "$E_{20}$" is changed into "A-B". It should be noted that "A" indicates the maximum gradation value.

Figure 7B:
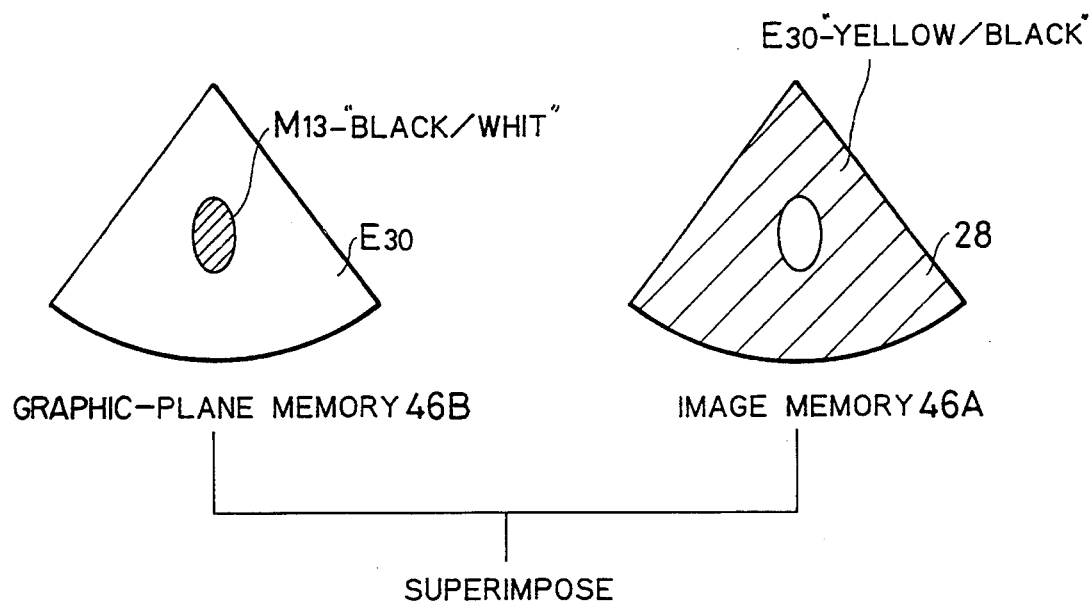

Finally, when displaying the effective region pattern "$M_{13}$" shown in FIG. 6C, all of the pixel points within the pattern "$M_{13}$" are represented as black/white patterns and all of the pixel points within the region "$E_{30}$" are represented as yellow/black patterns, as illustrated in FIG. 7B.

ARRANGEMENT OF SECOND SHOCKWAVE GENERATING APPARATUS WITH X-RAY SOURCE

Figure 8:
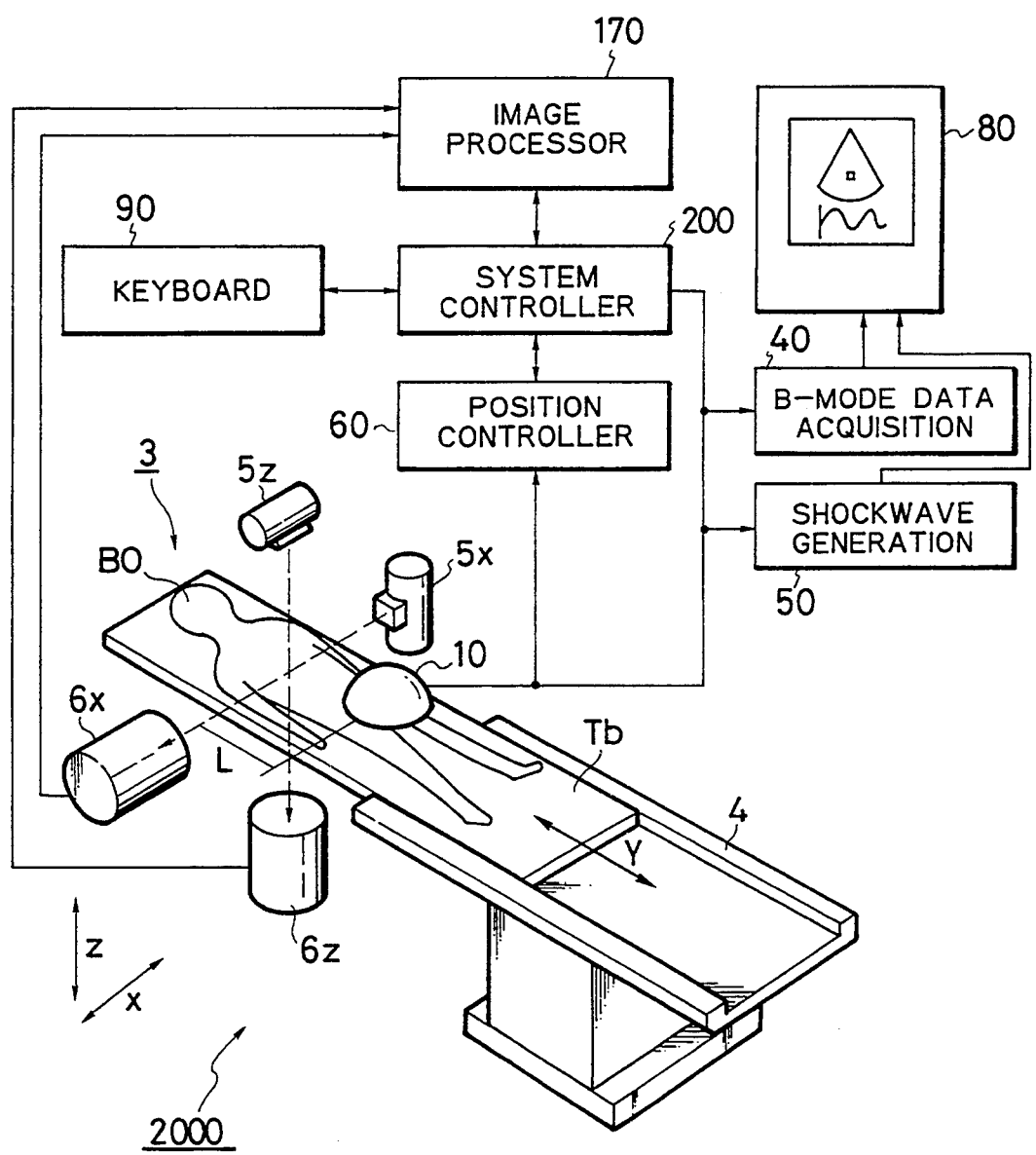
FIG. 8 is a schematic block diagram for showing an arrangement of a shockwave generating apparatus 2000 equipped with an X-ray source, according to a second preferred embodiment of the present invention; and, FIGS. 9 to 11 pictorically illustrate how to achieve the focal-point positioning operation by the second shockwave generating apparatus 2000.

FIG. 8 is a schematic block diagram of a shockwave generating apparatus 2000 in combination with an X-ray source, according to a second preferred embodiment of the present invention.

As apparatus from of FIG. 8, the major arrangement of the second shockwave generating apparatus 2000 is similar to that of the first shockwave generating apparatus 1000 shown in FIG. 1. Accordingly, only different arrangement of the second shockwave generating apparatus 2000 will now be described. That is, an X-ray imaging means 3 is provided to display an object to be cured by the shockwaves as an X-ray image. The X-ray imaging means 3 is constructed of a first X-ray generating unit "5X" arranged in an X direction; a first X-ray detecting unit "6X" such as an image intensifier positioned opposite to the X-ray generating unit 5X via a biological body "BO"; a second X-ray generating unit "5Z" arranged in a Z direction; and also a second X-ray detecting unit "6Z". It should be noted that these units 5X, 5Z, 6X and 6Z of the X-ray imaging means 3 are controlled by a system controller 200 having similar functions to those of the first-mentioned system controller 100.

Furthermore, an image processor 170 is employed in the second shockwave generating apparatus 2000 so as to process both X-ray imaging information and B-mode tomographic information. Also, a couch 4 is employed on which a table "Tb" with the biological body "BO" is slidable along a longitudinal direction "Y" thereof.

The X-ray imaging data obtained by the X-ray imaging means 3 are supplied to an image processor unit 170, so that the X-ray imaging data are processed to reconstruct a two-dimensional image in both the X direction and Z direction with respect to a preselected reference position, for instance, a position of the table "Tb". Then, the two-dimensional X-ray image of the biological body "BO" with an X-ray image of an object to be destroyed, e.g., a renal calculus, is displayed on the display unit 80.

FOCAL-POINT POSITIONING BY SECOND SHOCKWAVE GENERATING APPARATUS

Figure 9:
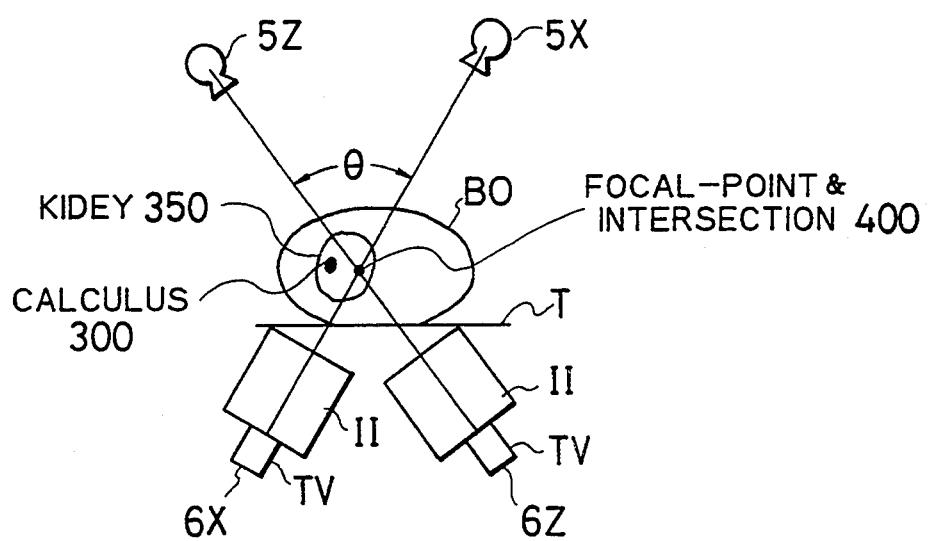
Figure 10A:
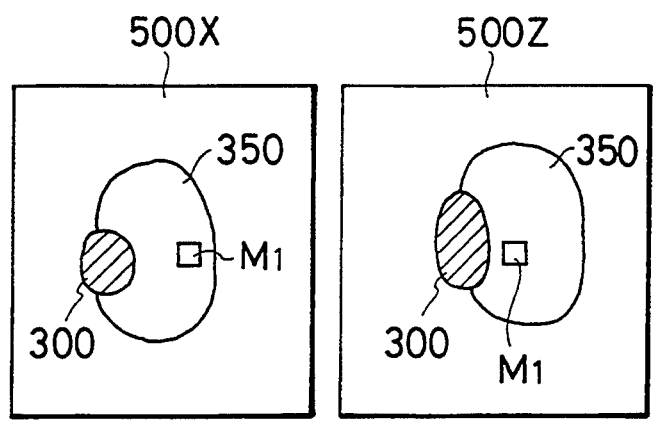
Figure 10B:
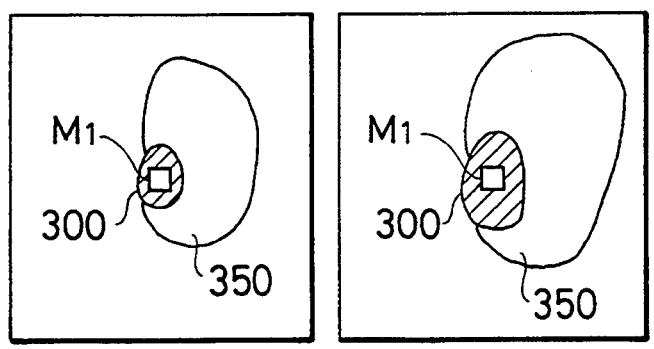
Figure 11:
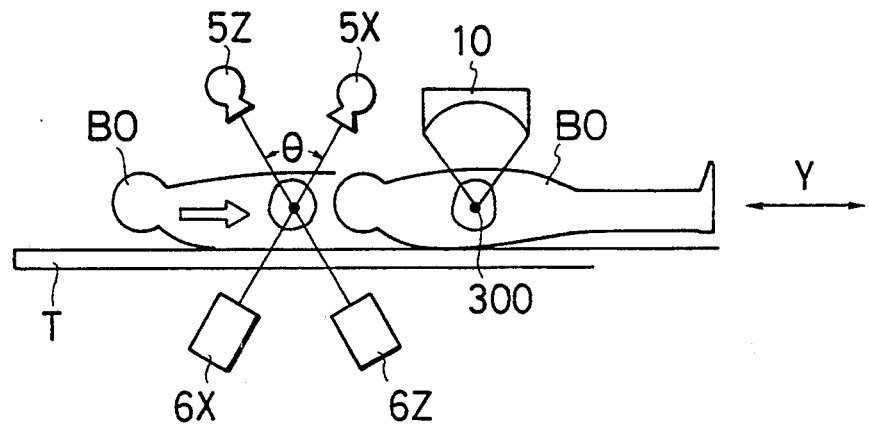

Referring now to FIGS. 9 to 11, a focal-point positioning operation according to the second shockwave generating apparatus 2000 will be pictorically described.

FIG. 9 illustrates a relative relationship between the first and second X-ray generating units 5X, 5Z, and the first and second X-ray detecting units 6X, 6Z with respect to the biological body "BO" containing a calculus 300 in its kidney 350. It is assumed that a intersection 400 between the X-ray emitted from the first and second X-ray generating units 5X and 5Z corresponds to a focal point thereof within the kidney 350. Each of the first and second X-ray detecting units 6X and 6Z is arranged by an image intensifier "TI" and an X-ray camera "TV".

When the X-ray imaging unit 3 is operated under the above-described conditions, two different X-ray images 500X and 500Z are obtained and displayed on the display screen of the display unit 80 in combination with, for example, the first effective region pattern "M₁", as represented in FIG. 10A. As apparent from these X-ray images 500X and 500Z, the center of the calculus 300 is not coincident with the center of the first shockwave effective region pattern "M₁".

Subsequently, as shown in FIG. 11, the table "Tb" on which the biological body "BO" is mounted is translated along the direction "Y" so as to position the calculus 300 within the first shockwave effective region pattern "M₁" as illustrated in FIG. 10B. As a consequence, the focal-point positioning operation of the second shockwave generating apparatus 2000 may be achieved.

It should be noted that the system controller 200 also has a function to detect positions of the X-ray imaging means 3. Although the table "Tb" has been translated in the above-described preferred embodiment, the shockwave applicator 10 may be alternatively translated under control of the position controller 60 so as to make the calculus 300 coincident with the shockwave effective region pattern "M₁".

Accordingly, the second shockwave generating apparatus 2000 may have the same advantages as those of the first shockwave generating apparatus 1000.

MODIFICATIONS

As apparent from the foregoing descriptions, the present invention is not limited to the above-described preferred embodiments, but may be modified without departing from the technical scope and spirit of the present invention.

For instance, the destroying transducer group 11 employed in the shockwave transducer may be excited by the second pulser 53 or the like so as to also produce a continuous ultrasonic wave whereby an object may be destroyed by way of thermal energy generated by focusing the continuous ultrasonic wave onto this object, resulting in a hyperthermia apparatus (not shown in detail). In this hyperthermia apparatus, a "thermal effective region pattern" (not shown) is utilized instead of the above-described shockwave effective region pattern. Also, the pressure values of either the shockwaves or continuous ultrasonic wave were employed as the reference value to determine the effective region "Eh" in the above-described preferred embodiments. Alternatively, other physical values of the shockwaves or continuous ultrasonic waves, for instance, an amount of energy of the shockwaves or continuous ultrasonic waves, or an acoustic pressure value higher than half of a peak acoustic pressure value may be utilized as this reference value.

What is claimed is:

1. A shockwave generating apparatus comprising:
  imaging means for imaging an interior area of a biological body under medical examination, containing an object to be destroyed, thereby to produce an image of said interior area;
  shockwave generating means for generating shockwaves to be focused onto said object to be destroyed;
  a position controlling means for adjusting a position of said shockwave generating means for setting a focus position of said shockwaves in relation to said image of said interior area and for outputting positional information on said focus position;
  storage means for storing predetermined data on a shockwave effective region produced by receiving shockwaves exceeding a predetermined physical value, in which region damage, caused by said shockwaves exceeding said predetermined physical value, is done to said biological body;
  pattern producing means for producing a pattern indicative of at least the shockwave effective region of said shockwaves where said object could be effectively destroyed; and
  display means, connected to said position controlling means and said storage means, for displaying said image of said interior area and said pattern indicative of at least said shockwave effective region based on both said positional information and said shockwave effective region data, said pattern being superimposed on said image of said interior area of said biological body, wherein said pattern substantially surrounds an area of said shockwave effective region and wherein a portion of said interior area beneath an interior portion of said pattern may be unobstructively viewed.

2. A shockwave generating apparatus as claimed in claim 1, wherein said imaging means includes an ultrasonic imaging unit.

3. A shockwave generating apparatus as claimed in claim 1, wherein said shockwave effective region pattern has a rectangular shape and substantially surrounds an overall area of said shockwave effective region.

4. A shockwave generating apparatus as claimed in claim 3, wherein a longitudinal length of said shockwave effective region pattern is between approximately 3 to 5 mm, and a transverse length thereof is selected between approximately 20 to 30 mm.

5. A shockwave generating apparatus as claimed in claim 1, wherein said shockwave effective region pattern has an elliptic shape, and substantially surrounds an outer line of said shockwave effective region.

6. A shockwave generating apparatus as claimed in claim 5, wherein said elliptic effective region pattern has a black/white combination pattern.

7. A method of removing a calculus comprising the steps of:
generating an image of an interior area of a biological body containing said calculus;
generating shockwaves to be focused onto said calculus;
setting a focus position of said shockwaves in relation to said image of said interior area;
detecting shockwaves returning from said biological body having a predetermined physical value which would result in damage to said biological body;
producing a pattern indicative of at least a shockwave effective region of said shockwaves where said calculus could be effectively disintegrated; and
displaying simultaneously said image of said interior area and said pattern indicative of at least said shockwave effective region based on said focus position and said detected shockwaves said pattern being superimposed on said image of said interior area of said biological body, said pattern substantially surrounding an area of said shockwave effective region such that a portion of said interior area beneath an interior portion of said pattern may be unobstructively viewed.

8. A hyperthermia generating apparatus comprising:
imaging means for imaging an interior area of a biological body under medical examination containing an object to be heated, thereby to produce an image of said interior area;
continuous ultrasonic-wave generating means for generating a continuous ultrasonic wave to be focused onto said object to be heated;
positioning means for setting a focus position of said continuous ultrasonic wave in relation to said image of said interior area and outputting positional information on said focus position;
storage means for storing predetermined data on a thermal effective region produced by receiving said continuous ultrasonic wave exceeding a predetermined physical value, in which region damage, caused by said continuous ultrasonic wave having said predetermined physical value, is done to said biological body;
pattern producing means for producing a pattern indicating said thermal effective region, said pattern substantially surrounding an area of said thermal effective region; and
display means for displaying said image of said interior area and said pattern indicative of said thermal effective region based on both said positional information and said thermal effective region data, said pattern being superimposed on said image of said interior area of said biological body such that a portion of said image of said interior area beneath an interior portion of said pattern may be unobstructively viewed.

9. A hyperthermia apparatus as claimed in claim 8, wherein said imaging means includes an ultrasonic imaging unit.

10. A hyperthermia apparatus as claimed in claim 8, wherein said thermal effective region pattern has a rectangular shape and substantially surrounds an overall area of said ultrasonic effective region.

11. A hyperthermia apparatus as claimed in claim 10, wherein a longitudinal length of said thermal effective region pattern is between approximately 3 to 5 mm, and a transverse length thereof is between approximately 20 to 30 mm.

12. A hyperthermia apparatus as claimed in claim 8, wherein said thermal effective region pattern has an elliptic shape, and substantially surrounds an outer line of said thermal effective region.

13. A hyperthermia apparatus as claimed in claim 12, wherein said elliptic effective region pattern has a black/white combination pattern.

* * * * *